United States Patent [19]
Denzel et al.

[11] 3,985,757
[45] Oct. 12, 1976

[54] PYRAZOLOPYRIDINE KETONES

[75] Inventors: Theodor Denzel, Regensburg; Hans Hoehn, Tegernheim, both of Germany

[73] Assignee: E. R. Squibb & Sons, Inc., Princeton, N.J.

[22] Filed: Sept. 17, 1975

[21] Appl. No.: 614,392

[52] U.S. Cl. .................... 260/294.8 C; 260/250 A; 260/256.4 R; 260/268 BC; 260/293.7; 260/295 S; 260/296 H; 424/263; 424/267
[51] Int. Cl.² ........................................ C07D 213/50
[58] Field of Search ............... 260/294.8 C, 296 H, 260/294.8 R, 295 S

[56] References Cited
UNITED STATES PATENTS

| | | | |
|---|---|---|---|
| 3,828,057 | 8/1974 | Denzel et al. | 260/296 H |
| 3,850,940 | 11/1974 | Denzel et al. | 260/294.9 |
| 3,862,947 | 1/1975 | Denzel et al. | 260/295.5 B |
| 3,925,388 | 12/1975 | Hoehn et al. | 260/268 BC |

*Primary Examiner*—Alan L. Rotman
*Attorney, Agent, or Firm*—Lawrence S. Levinson; Merle J. Smith

[57] ABSTRACT

New pyrazolo[3,4-b]pyridine-5-ketones having the general formula

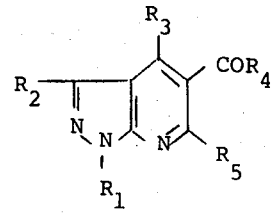

as well as their salts are useful as antiinflammatory agents and tranquilizers.

13 Claims, No Drawings

PYRAZOLOPYRIDINE KETONES

SUMMARY OF THE INVENTION

This invention relates to new pyrazolo [3,4-b]pyridine-5-ketones and salts. These new compounds have the formula

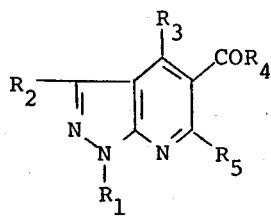

The symbols have the following meanings in formula I and throughout this specification. $R_1$ is hydrogen, lower alkyl, phenyl-lower alkylene. $R_2$ and $R_5$ each is hydrogen or lower alkyl. $R_3$ is hydroxy, lower alkoxy or the basic nitrogen group

wherein $R_6$ is hydrogen or lower alkyl and $R_7$ is hydrogen, lower alkyl, cyclo-lower alkyl, phenyl, phenyl-lower alkylene, or di-lower alkylamino-lower alkylene (except for lower alkyl, there is preferably only one of these substituent groups on the nitrogen). $R_4$ is one of the 5- or 6-membered heterocyclic radicals pyrrolidinyl, thienyl, furanyl, piperidinyl, pyrazolyl, pyrimidinyl, pyridyl, pyridazinyl or piperazinyl. The piperidine and piperazine may also bear as a substituent a hydroxy-lower alkyl group or one or two lower alkyl groups, e.g., (lower alkyl)-piperidinyl, di(lower alkyl)piperidinyl, (hydroxy-lower alkyl)piperazinyl, etc.

DETAILED DESCRIPTION OF THE INVENTION

The lower alkyl and lower alkylene groups in any of the foregoing radicals are straight or branched chain hydrocarbon groups of up to seven carbon atoms like methyl, ethyl, propyl, isopropyl, butyl, sec-butyl, t-butyl and the like. The lower alkoxy groups are of the same type like methoxy, ethoxy, propoxy, isopropoxy, etc. The $C_1-C_4$ members and especially $C_1-C_2$ members are preferred in each instance. Benzyl and phenethyl are the preferred phenyl-lower alkylene groups.

The basic nitrogen group

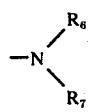

is an acyclic amino group wherein $R_6$ is hydrogen or lower alkyl and $R_7$ is hydrogen, lower alkyl, cyclo-lower alkyl, phenyl, phenyl-lower alkylene or di-loweralkylamino-lower alkylene (preferably there is only one of these substituents other than lower alkyl). These include, for example, amino, lower alkylamino, e.g., methylamino, ethylamino, etc., di(lower alkyl)amino, e.g., dimethylamino, methylethylamino diethylamino, etc., cyclo-lower alkylamino, e.g., cyclopropylamino, cyclobutylamino, cyclopentylamino, cyclohexylamino, etc., phenylamino, phenyl-lower alkylamino, e.g., benzylamino, phenethylamino, etc., di-lower alkylamino-lower alkylene, e.g., dimethylamino-methyl, dimethylaminoethyl, diethylaminoethyl, etc.

$R_4$ represents the nine heterocyclics named previously and the alkyl or (hydroxy-lower alkyl) members also identified. These heterocyclics can be attached by any carbon atom. Pyridyl and thienyl are preferred.

The cycloalkyl groups are the three to seven carbon alicyclics cyclopropyl, cyclobutyl, cyclopentyl, cyclohexyl and cycloheptyl of which the 3-, 5- and 6-membered rings are preferred.

The products of the examples are representative of the various compounds of this invention and constitute preferred embodiments. They also serve as models for other members. Especially preferred compounds of formula I are those wherein $R_1$ is hydrogen or lower alkyl, particularly ethyl; $R_2$ and $R_5$ each is hydrogen or lower alkyl, particularly methyl or ethyl, and especially hydrogen; $R_3$ is hydroxy, amino, lower alkoxy, especially ethoxy, lower alkylamino, especially butylamino or propylamino or cyclo-lower alkyl amino, especially $C_3$, $C_5$ and $C_6$-cyclo-lower alkylamino and most especially cyclopropylamino; and $R_4$ is thienyl or pyridyl.

The new compounds of formula I are formed by the following series of reactions. The symbols in the structural formulas have the same meaning as previously described.

A 5-aminopyrazole of the formula

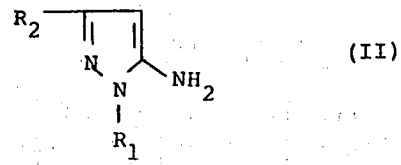

[produced analogous to the procedure described in Z.f. Chemie 10, 386, (1970)], is made to react with an alkoxymethylene aceto acetic acid of the formula

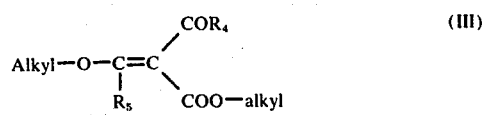

by heating at a temperature of about 120–130° C.

The resulting compound of the formula

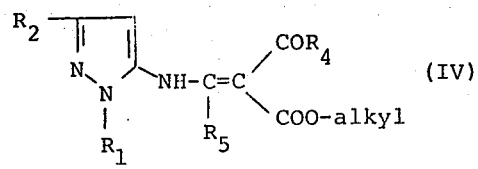

is cyclized in an inert organic solvent such as diphenyl ether at about 230° to about 260° C. while distilling off the alcohol formed, producing a compound of the formula

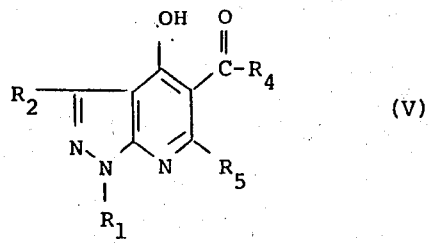

(V)

The compound of formula V is then treated with an alkylating agent, e.g., an alkyl halide like ethyl iodide, to form a compound of the formula

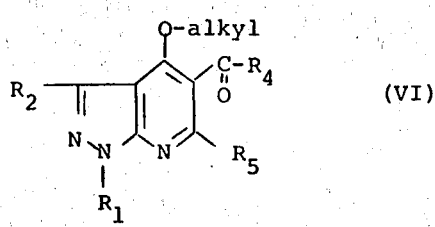

(VI)

The product of formula VI is then treated with a primary or secondary amine

at room or elevated temperature, e.g., up to reflux temperature for several hours, e.g., up to about 10–12 hours to obtain a product of formula I wherein $R_3$ is an amino substituent.

When $R_1$ is hydrogen, the foregoing procedure is modified by starting with a 5-aminopyrazole of formula II, wherein $R_1$ is an arylmethyl group, or a heteromethyl group. This starting material has the formula

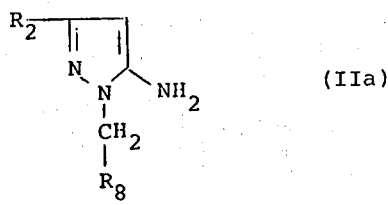

(IIa)

wherein $R_8$ is an aromatic or heterocyclic nucleus like phenyl, furyl, pyridyl, pyrimidyl, pyrazinyl or the like. The furanylmethyl group

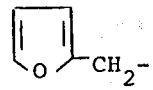

is preferred for $R_8$—CH$_2$—.

This material is processed through the reactions described above until the product corresponding to formula VI is obtained. At this point, the compound of formula VI wherein $R_1$ is the group $R_8$—CH$_2$—, e.g., furanylmethyl, is oxidized with an oxidizing agent like selenium dioxide in a high boiling solvent like diethyleneglycol dimethyl ether at about 160° C. or hydrolyzed by concentrated acid, e.g., sulfuric acid. This yields a compound of the formula

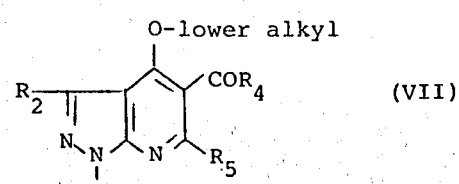

(VII)

and this product is treated with the amine as described above.

The compounds of formula I form salts which are also part of this invention. The salts include acid-addition salts, particularly the non-toxic, physiologically acceptable members. The bases of formula I form salts by reaction with a variety of inorganic and organic acids providing acid addition salts including, for example, the hydrohalides (especially the hydrochloride), sulfate, nitrate, phosphate, oxalate, tartrate, maleate, citrate, acetate, ascorbate, succinate, benzenesulfonate, toluenesulfonate, cyclohexanesulfonate, cyclohexanesulfamate, etc. The acid addition salts frequently provide a convenient means for isolating the product, e.g., by forming and precipitating the salt (not necessarily a physiologically acceptable salt) in an appropriate medium in which the salt is insoluble, then after separation of the salt, neutralizing with a base such as barium hydroxide or sodium hydroxide, to obtain the free base of formula I. Other salts can then be formed from the free base by reaction with an equivalent of acid containing the desired acid ion.

The new compounds of this invention have anti-inflammatory properties and are useful as anti-inflammatory agents, for example, to reduce local inflammatory conditions such as those of an edematous nature or resulting from proliferation of connective tissue in various mammalian species such as rats, dogs and the like when given orally in dosages of about 5 to 50 mg/kg/day, preferably 5 to 25 mg/kg/day, in single or 2 to 4 divided doses, as indicated by the carageenan edema assay in rats. The active substance is utilized in a dosage form such as tablet, capsule, solution or suspension containing up to about 300 mg. per unit of dosage of a compound or mixture of compounds of formula I or physiologically acceptable acid addition salt thereof. The active material is compounded in conventional manner with a physiologically acceptable vehicle or carrier, excipient, binder, preservative, stabilizer, flavor, etc. as called for by accepted pharmaceutical practice. Topical preparations, containing about 0.01 to 3 percent by weight of active substance, are formulated in a conventional lotion, salve or cream for topical application.

The new compounds of this invention also show central nervous system depressant activity and are useful as tranquilizers or ataractic agents for the relief of anxiety and tension states, for example, in mice, cats, rats, dogs and other mammalian species. For this purpose a compound or mixture of compounds of formula I, or non-toxic, physiologically acceptable acid addition salt thereof, is administered orally or parenterally in a conventional dosage form such as tablet, capsule, injectable or the like. A single dose, or preferably 2 to 4 divided doses, provided on a basis of about 10 to 50 mg. per kg. per day, preferably about 10 to 25 mg. per kg. per day, is appropriate. These are conventionally formulated in an oral or parenteral dosage form by compounding about 25 to 250 mg. per unit of dosage with conventional vehicle, excipient, binder, preservative, stabilizer, flavor or the like as called for by accepted pharmaceutical practice.

The following examples are illustrative of the invention. All temperatures are in degrees celsius.

EXAMPLE 1

[1-(2-Furanylmethyl)-4-hydroxy-1H-pyrazolo[3,4-b]pyridin-5-yl]-3-pyridylmethanone a.

α-[[[1-(2-furanylmethyl)-1H-pyrazol-5-yl]amino]methylene]-β-oxo-3-pyridinepropanoic acid, ethyl ester 32.2 g. of 5-amino-1-(2-furanylmethyl)pyrazole (0.02 mol.) are treated with 49.8 g. of ethoxymethylene-3-pyridinepropanoic acid (0.2 mol.) at 130° for 1 hour. After this time, the alcohol formed is removed in vacuo and the residue is crystallized by the addition of 100 ml. of ether, yield 66 g. (90%); m.p. 59°–61° b.

[1-(2-furanylmethyl)-4-hydroxy-1H-pyrazolo]3,4-b]pyridin-5-yl]-3-pyridylmethanone 7.3 g. of α-[[[1-(2-furanylmethyl)-1H-pyrazol-5-yl]amino]methylene]-β-oxo-3-pyridinepropanoic acid, ethyl ester (0.02 mol.) are heated in 20 ml. of diphenylether at 250° for 10 minutes. The mixture is cooled to room temperature and 20 ml. of ether are added. The product, [1-(2-furanylmethyl)-4-hydroxy-1H-pyrazolo]3,4-b]pyridin-5-yl]-3-pyridylmethanone precipitates and is recrystallized from butyl alcohol, yield 3.8 g. (60%); m.p. 152°–153°.

EXAMPLE 2

[1-(2-Furanylmethyl)-4-hydroxy-1H-pyrazolo[]3,4-b]pyridin-5-yl]-2-thienylmethanone a.

α-[[[1-(2-furanylmethyl)-1H-pyrazol-5-yl]amino]methylene]-β-oxo-2-thiophenepropanoic acid, ethyl ester 16.1 g. of 5-amino-1-(2-furanylmethyl)pyrazole (0.1 mol.) are treated with 25.8 g of ethoxymethylene-2-thiophenepropanoic acid ethyl ester at 140° for 30 minutes. The alcohol formed is distilled off in vacuo and the oily residue is crystallized with methanol, yield 32.6 g. (88%); m.p. 80°–82°.

b. [1-(2-furanylmethyl)-4-hydroxy-1H-pyrazolo[]3,4-b]pyridin-5-yl]-2-thienylmethanone 3.7 g. of α-[[[1-(2-Furanylmethyl)-1H-pyrazol-5-yl]amino]methylene]-β-oxo-2-thiophenepropanoic acid, ethyl ester (0.01 mol.) are heated for 3 minutes at 270°. After cooling to room temperature, methanol is added and the crystalline compound is filtered off, yield 2.8 g. (87%); m.p. 139°–141° (butanol).

EXAMPLE 3

[4-Ethoxy-1-(2-furanylmethyl)-1H-pyrazolo[3,4-b]pyridin-5-yl]-2-thienylmethanone 3.3 g. of [1-(2-furanylmethyl)-4-hydroxy-1H-pyrazolo[3,4-b]pyridine-5-yl]-2-thienylmethanone (0.01 mol.), 1.5 g. of potassium carbonate (0.011 mol.) and 3.1 g. of ethyl iodide (0.02 mol.) are stirred together in 20 ml. of dimethylformamide at 70° for 12 hours. After this time, the inorganic precipitate is filtered off and the filtrate treated with about 10 ml. of water. The product, [4-Ethoxy-1-(2-furanylmethyl)-1H-pyrazolo[3,4-b]pyridin-5-yl]-2-thienylmethanone, crystallizes on standing, yield 3 g. (86%); m.p. 85°–87° (methanol).

EXAMPLE 4

(4-Ethoxy-1H-pyrazolo[3,4-b]pyridin-5-yl)-2-thienylmethanone 3.5 g. of [4-ethoxy-1-(2-furanylmethyl)-1H-pyrazolo[3,4-b]pyridin-5-yl]-2-thienylmethanone (0.01 mol.) are treated with 1.22 g. of selenium dioxide (0.011 mol.) in 20 ml. of diethyleneglycol dimethylether at reflux temperature for 1.5 hours with stirring. The precipitated selenium is filtered off and the solution is evaporated to dryness in vacuo. The remaining product, (4-ethoxy-1H-pyrazolo[3,4-b]pyridin-5-yl]-2-thienylmethanone, is recrystallized from butanol, yield 2 g. (75%); m.p. 202°–205°.

EXAMPLE 5

[4-[(1-methylpropyl)amino]-1H-pyrazolo]3,4-b]pyridin-5-yl]-2-thienylmethanone 2.7 g. of (4-ethoxy-1H-pyrazolo[3,4-b]pyridin-5-yl)-2-thienylmethanone (0.01 mol.) are refluxed in 20 ml of sec. butylamine with stirring for 10 hours. The excess amine is distilled off and the residual product, [4-[(1-methylpropyl)amino]-1H-pyrazolo[3,4-b]pyridin-5-yl]--yl]--thienylmethanone is recrystallized from ethanol yield 2.5 g. (83%); m.p. 194°–196°.

EXAMPLE 6

[4-(Cyclopropylamino)-1H-pyrazolo[3,4-b]pyridin-5-yl]-2-thienylmethanone

By substituting cyclopropylamine for the sec. butylamine in the procedure of Example 5, [4-(cyclopropylamino)-1H-pyrazolo[3,4-b]pyridin-5-yl]-2-thienylmethanone is obtained, yield 78%; m.p. 268°–270° (butanol). Treatment of the product with HCl saturated methanol and addition of ether yields the hydrochloride salt.

EXAMPLE 7

[4-[1-(methylethyl)amino]-1H-pyrazolo[3,4-b]pyridin-5-yl]-2-thienylmethanone

By substituting isopropylamine for the sec. butylamine in the procedure of Example 5, [4-[1-(methylethyl)amino]-1H-pyrazolo[3,4-b]pyridin-5-yl]-2-thienylmethanone is obtained, yield 82%, m.p. 229°–231° (butanol).

EXAMPLE 8

(4-Amino-1H-pyrazolo[3,4-b]pyridin-5-yl)-2-thienylmethanone

By substituting ammonia solution for the sec-butylamine in the procedure of Example 5, (4-amino-1H-pyrazolo[3,4-b] pyridin-5-yl)-2-thienylmethanone is obtained, yield 68%; m.p. 282–284%; (DMF).

EXAMPLE 9

[4-Ethoxy-1-(2-furanylmethyl)-1H-pyrazolo[3,4-b]pyridin-5-yl]-3-pyridylmethanone By treating the product of Example 1b with potassium carbonate and ethyl iodide as in Example 3, [4-ethoxy-1-(2-furanylmethyl)-1H-pyrazolo[]3,4-b]pyridin-5-yl-3-pyridylmethanone is obtained.

EXAMPLE 10

(4-Ethoxy-1H-pyrazolo[3,4-b]pyridin-5-yl)-3-pyridylmethanone

By treating the product of Example 9 with selenium dioxide in diethyleneglycol dimethylether as in Example 4, (4-ethoxy-1H-pyrazolo[3,4-b]pyridin-5-yl]-3-pyridylmethanone is obtained.

EXAMPLE 11

[4-(Phenylamino)]-1H-pyrazolo[3,4-b]pyridin-5-yl)-3-pyridylmethanone

The product of Example 10 is treated with aniline instead of sec-butylamine according to the procedure of Example 5 and [4-(phenylamino)]-1H-pyrazolo[3,4-b]pyridin-5-yl)-3-pyridylmethanone is obtained.

EXAMPLE 12

By substituting ethoxymethylene-4-pyridinepropanoic acid as starting material in Example 1a, then proceeding as in Examples 1b, 9, 10 and 11, the following products are obtained, respectively:

α-[[[1-(2-furanylmethyl)-1H-pyrazol-5-yl]amino]methylene]-β-oxo-4-pyridine propanoic acid, ethyl ester.

[1-(2-furanylmethyl)-4-hydroxy-1H-pyrazolo[3,4-b]pyridin-5-yl]-4-pyridylmethanone.

[4-ethoxy-1-(2-furanylmethyl)-1H-pyrazolo[3,4-b]pyrid-5-yl]-4-pyridinylmethanone.

(4-ethoxy-1H-pyrazolo[3,4-b]pyridin-5-yl)-4-pyridylmethanone.

[4-(phenylamino)]-1H-pyrazolo[3,4-b]pyridin-5-yl)-4-pyridylmethanone.

EXAMPLE 13

By substituting 5-amino-1-ethylpyrazole for the 5-amino-1-(2-furanylmethyl)pyrazole and ethoxymethylene-3-thiophenepropanoic acid ethyl ester for the ethoxymethylene-2-thiophenepropanoic acid ethyl ester in the procedure of Example 2a then proceeding as in Example 2b, 3, 5, 6, 7 and 8, the following products are obtained respectively:

α-[[[1-ethyl-1H-pyrazol-5-yl]amino]methylene]-β-oxo-3-thiophenepropanoic acid, ethyl ester.

[1-ethyl-4-hydroxy-1H-pyrazolo[3,4-b]pyridin-5-yl]-3-thienylmethanone.

[4-ethoxy-1-ethyl-1H-pyrazolo[3,4-b]pyridin-5-yl]-3-thienylmethanone.

[1-ethyl-4-[(1-methylpropyl)amino]-1H-pyrazolo[3,4-b]pyridin-5-yl]-3-thienylmethanone.

[4-(cyclopropylamino)-1-ethyl-1H-pyrazolo[3,4-b]pyridin-5-yl]-3-thienylmethanone.

[1-ethyl-4-[1-(methylethyl)amino]-1H-pyrazolo[3,4-b]pyridin-5-yl-3-thienylmethanone.

(4-amino-1-ethyl-1H-pyrazolo[3,4-b]pyridin-5-yl)-3-thienylmethanone.

The following products are obtained by following the procedure of Example 2 substituting for the 5-amino-1-(2-furanylmethyl)pyrazole in part a the 1-$R_1$, 3-$R_2$ 5-amino-pyrazole having the $R_1$ and $R_2$ substituents indicated below (except when $R_1$ is hydrogen, a 3-$R_2$-5-amino-1-(2-furanylmethyl)-pyrazole is used) and substituting in that part for the ethoxymethylene-2-thiophenepropanoic acid ethyl ester the ester of formula III having the $R_4$ and $R_5$ substituents indicated below, then following the procedures of Examples 3 and 5 (adding the step of Example 4 when $R_1$ is hydrogen) substituting for the sec. butylamine in Example 5 the amine

having the $R_6$ and $R_7$ substituents indicated below:

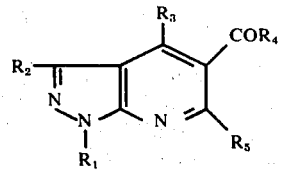

| Example | $R_1$ | $R_2$ | $R_3$ | $R_4$ | $R_5$ |
|---|---|---|---|---|---|
| 14 | ⌬-CH₂— | —CH₃ | —OH | (thienyl) | H |

-continued
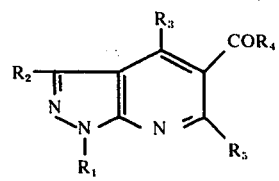
| Example | $R_1$ | $R_2$ | $R_3$ | $R_4$ | $R_5$ |
|---|---|---|---|---|---|
| 15 | C₆H₅-C₂H₄- | H | -OH | 2-pyridyl | -CH₃ |
| 16 | C₆H₅-CH₂- | -CH₃ | -OC₃H₇ | 2-thienyl | H |
| 17 | C₆H₅-CH₂- | -CH₃ | -N(C₂H₅)₂ | 2-thienyl | H |
| 18 | H | -CH₃ | -OH | 2-thienyl | -CH₃ |
| 19 | H | -CH₃ | -OCH₃ | 2-thienyl | -CH₃ |
| 20 | H | -CH₃ | -NH-cyclopentyl | 2-thienyl | -CH₃ |
| 21 | -C₂H₅ | -CH₃ | -OH | 3-pyridyl | -CH₃ |
| 22 | -C₂H₅ | -CH₃ | -OC₄H₉ | 3-pyridyl | -CH₃ |
| 23 | -C₂H₅ | -CH₃ | -NHCH₃ | 3-pyridyl | -CH₃ |
| 24 | -C₄H₉ | H | -OH | 2-thienyl | H |
| 25 | -C₄H₉ | H | -OC₂H₅ | 2-thienyl | H |
| 26 | -C₄H₉ | H | -NH-cyclohexyl | 2-thienyl | H |
| 27 | H | -C₄H₉ | -OH | 3-pyridyl | H |

-continued

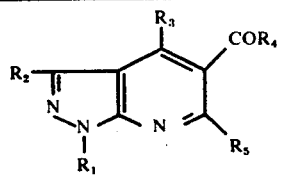

| Example | R₁ | R₂ | R₃ | R₄ | R₅ |
|---|---|---|---|---|---|
| 28 | H | —C₄H₉ | —OC₂H₅ | 3-pyridyl | H |
| 29 | H | —C₄H₉ | N(CH₃)₂ | 3-pyridyl | H |
| 30 | —C₂H₅ | H | —OH | 4-pyridyl | —C₄H₉ |
| 31 | —C₂H₅ | H | —OC₂H₅ | 4-pyridyl | —C₄H₉ |
| 32 | —C₂H₅ | H | —NH(CH₂)₂-phenyl | 4-pyridyl | —C₄H₉ |
| 33 | H | H | —NH(CH₂)₂N(CH₃)₂ | 2-thienyl | H |
| 34 | H | H | —NH(CH₂)₃N(C₂H₅)₂ | 3-pyridyl | H |
| 35 | —C₂H₅ | —CH₃ | —NHCH₂N(CH₃)₂ | 2-thienyl | —CH₃ |
| 36 | H | —CH₃ | —NH-phenyl | 2-thienyl | —CH₃ |
| 37 | H | H | —OH | 2-furyl | H |
| 38 | H | H | —OCH₃ | 2-furyl | H |
| 39 | H | H | —NHC₃H₇ | 2-furyl | H |
| 40 | —C₂H₅ | H | —OH | 2-pyrrolidinyl | H |
| 41 | —C₂H₅ | H | —OC₂H₅ | 2-pyrrolidinyl | H |

-continued
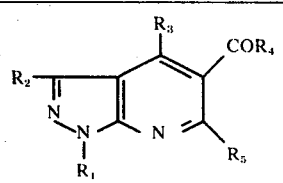
| Example | $R_1$ | $R_2$ | $R_3$ | $R_4$ | $R_5$ |
|---|---|---|---|---|---|
| 42 | —$C_2H_5$ | H | —$NHC_2H_5$ | pyrrolidinyl | H |
| 43 | H | H | —OH | pyrazolyl | H |
| 44 | H | H | —$OCH_3$ | pyrazolyl | H |
| 45 | H | H | —$NHC_2H_5$ | pyrazolyl | H |
| 46 | H | H | —OH | piperidinyl | H |
| 47 | H | H | —$OC_2H_5$ | piperidinyl | H |
| 48 | H | H | —NH—C$_6$H$_5$ | piperidinyl | H |
| 49 | $C_2H_5$ | —$CH_3$ | —OH | $(CH_2)_2OH$ piperazinyl | H |
| 50 | $C_2H_5$ | —$CH_3$ | $OC_2H_5$ | $(CH_2)_2OH$ piperazinyl | H |
| 51 | $C_2H_5$ | —$CH_3$ | —$N(CH_3)_2$ | $(CH_2)_2OH$ piperazinyl | H |
| 52 | H | H | —OH | 4-methylpiperidinyl | $CH_3$ |

-continued

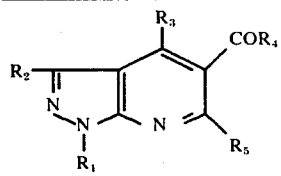

| Example | R₁ | R₂ | R₃ | R₄ | R₅ |
|---|---|---|---|---|---|
| 53 | H | H | —OCH₃ | 4-methylpiperidinyl | CH₃ |
| 54 | H | H | —NH₂ | 4-methylpiperidinyl | CH₃ |
| 55 | C₂H₅ | CH₃ | —OH | pyrimidinyl | H |
| 56 | C₂H₅ | CH₃ | —OC₂H₅ | pyrimidinyl | H |
| 57 | C₂H₅ | CH₃ | —NH—cyclopropyl | pyrimidinyl | H |
| 58 | H | H | —OH | pyridazinyl | H |
| 59 | H | H | —OC₃H₇ | pyridazinyl | H |
| 60 | H | H | —NCH₃H₇ | pyridazinyl | H |
| 61 | H | H | —OH | pyridyl | |
| 62 | H | H | —OC₂H₅ | pyridyl | |
| 63 | H | H | —NHCH₃ | pyridyl | |
| 64 | C₂H₅ | CH₃ | —NH(C₂H₅)₂ | pyridyl | |

What is claimed is:

1. A compound of the formula

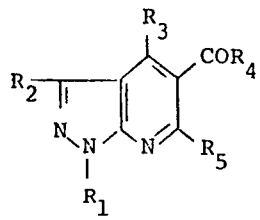

wherein $R_1$ is hydrogen, lower alkyl or phenyl-lower alkylene; $R_2$ and $R_5$ each is hydrogen or lower alkyl; $R_3$ is hydroxy, lower alkoxy or

wherein $R_6$ is hydrogen or lower alkyl and $R_7$ is hydrogen, lower alkyl, cyclo-lower alkyl, phenyl, phenyl-lower alkylene or di-lower alkylamino-lower alkylene; $R_4$ is thienyl, furanyl, or pyridyl and physiologically acceptable acid addition salts thereof.

2. A compound as in claim 1 wherein $R_4$ is pyridyl.
3. A compound as in claim 1 wherein $R_4$ is thienyl.
4. A compound of the formula

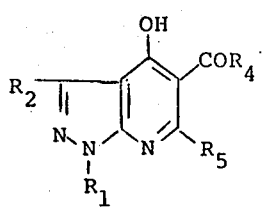

wherein $R_1$, $R_2$, $R_4$ and $R_5$ have the same meaning as in claim 1.

5. A compound of the formula

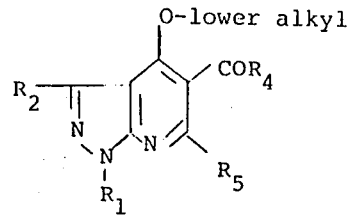

wherein $R_1$, $R_2$, $R_4$ and $R_5$ have the same meaning as in claim 1.

6. A compound of the formula

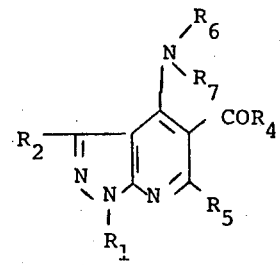

wherein $R_1$ is hydrogen, lower alkyl, benzyl or phenethyl; $R_2$, $R_5$ and $R_6$ each is hydrogen or lower alkyl; $R_4$ is thienyl, pyridyl or furanyl; $R_7$ is hydrogen, lower alkyl, cyclo-lower alkyl, phenyl, benzyl, phenethyl or di-lower alkylamino-lower alkylene; and physiologically acceptable acid addition salts thereof.

7. A compound as in claim 6 wherein $R_4$ is pyridyl.
8. A compound as in claim 6 wherein $R_4$ is thienyl.
9. A compound as in claim 6 having the name [4-[(1-methylpropyl)amino]-1H-pyrazolo[3,4-b]pyridin-5-yl]-2-thienylmethanone.
10. A compound as in claim 6 having the name [4-(cyclopropylamino)-1H-pyrazolo[3,4-b]pyridin-5-yl]-2-thienylmethanone.
11. A compound as in claim 6 having the name [4-[1-(methylethyl)amino]-1H-pyrazolo[3,4-b]pyridin-5-yl]-2-thienylmethanone.
12. A compound as in claim 6 having the name (4-amino-1H-pyrazolo[3,4-b]pyridin-5-yl)-2-thienylmethanone.
13. A compound as in claim 7 wherein $R_1$, $R_2$, $R_5$ and $R_6$ each is hydrogen and $R_7$ is lower alkyl or cyclo-lower alkyl.

* * * * *